United States Patent [19]
Van den Berg et al.
[11] Plant 4,734
[45] Jun. 2, 1981

[54] KALANCHOE PLANT

[75] Inventors: Cornelis P. Van den Berg; James C. Mikkelsen, both of Ashtabula, Ohio

[73] Assignee: Mikkelsens, Inc., Ashtabula, Ohio

[21] Appl. No.: 134,115

[22] Filed: Mar. 26, 1980

[51] Int. Cl.³ ..... A01H 5/00
[52] U.S. Cl. ..... Plt./68
[58] Field of Search ..... Plt./68

*Primary Examiner*—James R. Feyrer
*Attorney, Agent, or Firm*—Schwartz, Jeffery, Schwaab, Mack, Blumenthal & Koch

[57] ABSTRACT

A new kalanchoe plant named Serenade, characterized by its early flowering, high degree of self-branching, bright red flower color, dense foliage, well clustered flowers, and floriferous habit.

1 Drawing Figure

1

The present invention relates to a new and distinctive variety of kalanchoe plant, botanically known as *Kalanchoe blossfeldiana Poelln*, and referred to by the cultivar name Serenade.

The new cultivar was developed by us through controlled breeding by self-pollinating Mikkelsen seedling No. 76-383-3. Asexual reproduction by stem cuttings has shown that the unique features of this new kalanchoe are stabilized and are reproduced true to type in successive propagations.

The following characteristics distinguish Serenade from both its parent cultivar and other cultivated kalanchoes of this type known and used in the floriculture industry:

1. Serenade is particularly characterized by and was selected for its high degree of self-branching, and early flowering habit.

2. Branching is slightly better than that of Feuerball disclosed in U.S. Plant Pat. No. 3,861, issued to Adolf Grob, and superior to that of most other cultivated Kalanchoes of this type known.

3. Plant growth is relatively slow, comparable to that of Feuerball.

4. Foliage is dense, small, with a pronounced crenate margin.

5. Growth rate, leaf size and self-branching makes Serenade especially suitable for production in 10–12 cm. pots.

6. After flower initiation plants must be treated with B9 in all seasons to reduce peduncle elongation.

7. Flowering time is 9 weeks in summer to 13 weeks in winter after start of short days, which is 2–3 weeks faster than Feuerball, as tested in Ashtabula, Ohio.

8. Well clustered flowers, and highly floriferous.

9. Flower color is bright red, with the flowers being approximately the same color and size as those of Feuerball.

10. Peduncles have a tendency to stretch and weaken under adverse growing conditions (low light intensity with high temperatures).

The accompanying colored photograph illustrates the overall appearance and color of Serenade. The photograph is a top perspective view and shows the flower and foliage colors as true as it is reasonably possible to obtain in a colored reproduction of this type.

The following is a detailed description of the new kalanchoe cultivar, based on plants produced under commercial practices in greenhouses of Mikkelsens Inc. in Ashtabula, Ohio. Color references are made to the Royal Horticultural Society Colour Chart except

2 where general terms of ordinary dictionary significance are used.

Parentage:

A controlled self-pollination of Mikkelsen seedling No. 76-383-3.

Propagation:

(A) *Type cutting.*—Short tip cutting, with stems up to 2 cm. long.

(B) *Time to root.*—10 days at 21° C. summer; 14 days at 21° C. winter.

(C) *Rooting habit.*—Abundant, fibrous, fine roots.

Plant description:

(A) *Form.*—Short, compact, upright. Growing and scheduling practices can produce a small plant in a 10 cm. pot or a larger plant in a 12 cm. pot.

(B) *Habit of growth.*—Rate of growth moderate for this type of plant; generally, shoots are formed at every node.

(C) *Foliage description.*—Leaves simple, opposite. (1) Size: Average full grown leaf of a flowering plant in a 10 cm. pot is 80 mm. long × 50 mm. wide. In plants grown under long days (stock plants), average full grown leaf is 100 mm. long × 70 mm. wide. (2) Shape: Elliptic to oblong, apex obtuse to acute, base attenuate. (3) Texture: Glabrous, coriaceous, succulent. (4) Margin: Pronounced crenate to dentate. (5) Color: Young foliage, top side yellow-green 147A, under side green 137B. Mature foliage, top side green 139A, under side green 137B.

Flowering description:

(A) *Flowering habits.*—Inflorescence of each shoot is formed by dichotomous branching, starting with opening of terminal flower of main axis, followed by terminal flowers of the side branches, continuing with subsequent development of branches in the inflorescence.

(B) *Natural flowering season.*—Early January. Flowering time under controlled daylength at 20° C. is 9 weeks in summer and 13 weeks in winter. Flowering time depends on temperature, light intensity and other growing conditions.

(C) *Flower bud description.*—Elliptical to oblong, up to 10 mm. long, developing to tubular as flower petals mature, sheathed with four green sepals. Corolla at maturity 8 mm. long.

(D) *Flowers borne.*—Compound dichasial cymes; primary peduncle 5 mm. in diameter, with peduncle length depending on growing conditions and B9 application; pedicels up to 5 mm. long.

(E) *Quantity of flowers.*—High floriferous; main axis counted over 100 flowers, side branches over 50 flowers, with 6–8 side branches in a 10 cm. potted plant.

(F) *Petals.*—(1) Shape: Nearly round, top cuspidate. (2) Color: Top side when opening red 44B, fading to red 40A; under side very light red infused with very light green. (3) Number of petals: 4, united in corolla, salverform; petals 5 mm. in diameter, total flowering diameter 13 mm.

(G) *Reproductive organs.*—(1) Stamens: Eight (8) in number. (a) Anther shape: Flat, elliptical; color yellow. (b) Filament color: Light green. (c) Pollen color: Yellow. (2) Pistils (a) Stigma shape: Flat, crystalline, color greenish white. (b) Style color: Light green. (c) Ovaries: 4 celled, size 4 mm. long, color light green.

Disease resistance:

No diseases or adverse physiological problems observed to date. Cultivar is highly resistant to mildew.

We claim:

1. A new and distinct cultivar of kalanchoe plant known by the cultivar name Serenade, as described and illustrated, and particularly characterized by its early flowering, high degree of self-branching, bright red flower color, dense foliage, and by its well clustered flowers and floriferous habit.

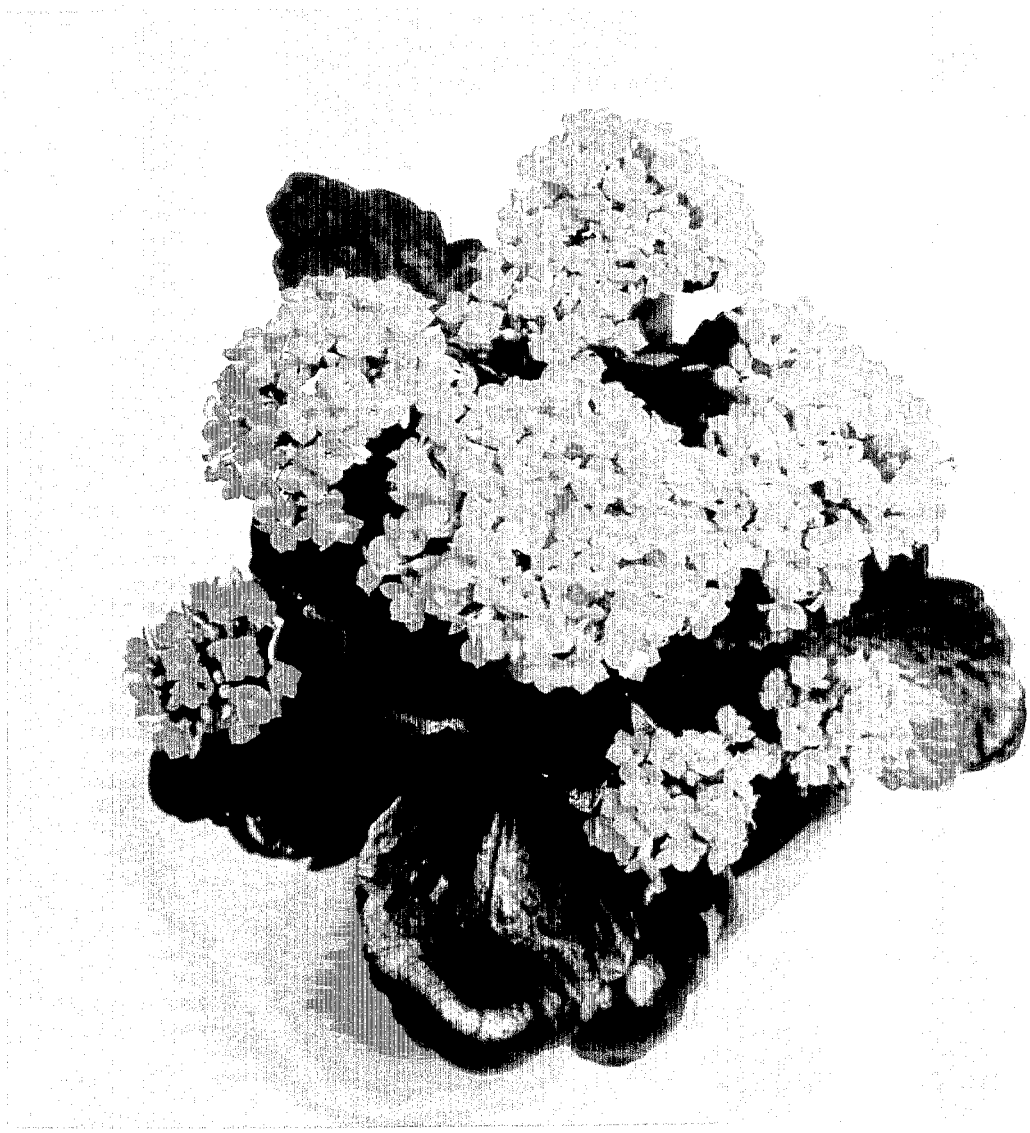

* * * * *